(12) United States Patent
Sathaye et al.

(10) Patent No.: US 8,948,867 B2
(45) Date of Patent: Feb. 3, 2015

(54) CAPTURE DETECTION WITH CROSS CHAMBER BACKUP PACING

(75) Inventors: Alok Sathaye, Minneapolis, MN (US); M. Jason Brooke, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1978 days.

(21) Appl. No.: 11/520,880

(22) Filed: Sep. 14, 2006

(65) Prior Publication Data

US 2008/0071319 A1    Mar. 20, 2008

(51) Int. Cl.
*A61N 1/362* (2006.01)
*A61N 1/37* (2006.01)

(52) U.S. Cl.
CPC ..................................... *A61N 1/371* (2013.01)
USPC ........... 607/28; 607/2; 607/9; 607/14; 607/27

(58) Field of Classification Search
USPC .............. 607/9, 15, 27, 28, 14; 600/516–517, 600/521
See application file for complete search history.

(56) References Cited

U.S. PATENT DOCUMENTS

| | | |
|---|---|---|
| 4,573,481 A | 3/1986 | Bullara |
| 5,033,467 A | 7/1991 | Bocchi et al. |
| 5,203,348 A | 4/1993 | Dahl et al. |
| 5,230,337 A | 7/1993 | Dahl et al. |
| 5,301,677 A | 4/1994 | Hsung |
| 5,350,410 A | 9/1994 | Kleks et al. |
| 5,360,442 A | 11/1994 | Dahl et al. |
| 5,366,496 A | 11/1994 | Dahl et al. |
| 5,372,606 A | 12/1994 | Lang et al. |
| 5,391,200 A | 2/1995 | Kenknight et al. |
| 5,397,342 A | 3/1995 | Heil, Jr. et al. |
| 5,411,525 A | 5/1995 | Swanson et al. |
| 5,431,693 A | 7/1995 | Schroeppel |
| 5,443,485 A | 8/1995 | Housworth |
| 5,468,254 A | 11/1995 | Hahn et al. |
| 5,480,414 A * | 1/1996 | Stroebel et al. ................. 607/28 |
| 5,545,186 A | 8/1996 | Olson et al. |

(Continued)

FOREIGN PATENT DOCUMENTS

| | | |
|---|---|---|
| WO | WO2004091720 | 10/2004 |
| WO | WO2007087025 | 8/2007 |

OTHER PUBLICATIONS

U.S. Appl. No. 12/154,410, filed May 22, 2008, Sathaye.

(Continued)

*Primary Examiner* — Carl H Layno
*Assistant Examiner* — Jennifer Ghand
(74) *Attorney, Agent, or Firm* — Seager, Tufte & Wickhem, LLC

(57) ABSTRACT

In connection with capture detection for a heart chamber with backup pacing in a contralateral heart chamber, a cardiac signal of the first heart chamber is sensed following delivery of a pacing pulse. The cardiac response of the first heart chamber to the pacing pulse is classified based on one or more features of the sensed cardiac signal. A backup pacing pulse is delivered to a second heart chamber contralateral to the first heart chamber. For example, the timing of the delivery of the backup pacing pulse may be based on the expected or detected timing of the features used to classify the cardiac pacing response. The backup pace may be delivered within a detection window used for sensing the features indicative of the cardiac pacing response.

23 Claims, 10 Drawing Sheets

(56) References Cited

U.S. PATENT DOCUMENTS

| | | | |
|---|---|---|---|
| 5,545,202 | A | 8/1996 | Dahl et al. |
| 5,591,216 | A | 1/1997 | Testerman et al. |
| 5,603,732 | A | 2/1997 | Dahl et al. |
| 5,634,938 | A | 6/1997 | Swanson et al. |
| 5,658,318 | A | 8/1997 | Stroetmann et al. |
| 5,674,254 | A | 10/1997 | van Krieken |
| 5,683,431 | A | 11/1997 | Wang |
| 5,697,956 | A | 12/1997 | Bornzin |
| 5,718,720 | A | 2/1998 | Prutchi et al. |
| 5,735,883 | A | 4/1998 | Paul et al. |
| 5,855,593 | A | 1/1999 | Olson et al. |
| 5,916,243 | A | 6/1999 | KenKnight et al. |
| 6,076,015 | A | 6/2000 | Hartley et al. |
| 6,141,581 | A | 10/2000 | Olson et al. |
| 6,148,234 | A | 11/2000 | Struble |
| 6,221,011 | B1 | 4/2001 | Bardy |
| 6,259,947 | B1 | 7/2001 | Olson et al. |
| 6,270,457 | B1 | 8/2001 | Bardy |
| 6,277,072 | B1 | 8/2001 | Bardy |
| 6,280,380 | B1 | 8/2001 | Bardy |
| 6,312,378 | B1 | 11/2001 | Bardy |
| 6,336,903 | B1 | 1/2002 | Bardy |
| 6,358,203 | B2 | 3/2002 | Bardy |
| 6,360,127 | B1 | 3/2002 | Ding et al. |
| 6,363,281 | B1 | 3/2002 | Zhu et al. |
| 6,368,284 | B1 | 4/2002 | Bardy |
| 6,398,728 | B1 | 6/2002 | Bardy |
| 6,434,428 | B1 | 8/2002 | Sloman et al. |
| 6,438,410 | B2 | 8/2002 | Hsu et al. |
| 6,440,066 | B1 | 8/2002 | Bardy |
| 6,487,443 | B2 | 11/2002 | Olson et al. |
| 6,493,586 | B1 | 12/2002 | Stahmann et al. |
| 6,512,953 | B2 | 1/2003 | Florio |
| 6,597,951 | B2 | 7/2003 | Kramer et al. |
| 6,611,712 | B2 | 8/2003 | Spinelli et al. |
| 6,615,089 | B1 | 9/2003 | Russie et al. |
| 6,640,136 | B1 | 10/2003 | Helland et al. |
| 6,708,058 | B2 | 3/2004 | Kim et al. |
| 6,731,985 | B2 | 5/2004 | Poore et al. |
| 6,738,668 | B1 | 5/2004 | Mouchawar et al. |
| 6,772,008 | B2 | 8/2004 | Zhu et al. |
| 6,915,160 | B2 | 7/2005 | Auricchio et al. |
| 6,915,164 | B2 | 7/2005 | Bradley et al. |
| 6,963,775 | B2 | 11/2005 | Russie et al. |
| 6,978,178 | B2 | 12/2005 | Sommer et al. |
| 6,993,389 | B2 | 1/2006 | Ding |
| 7,031,773 | B1 | 4/2006 | Levine et al. |
| 7,062,327 | B2 | 6/2006 | Bradley et al. |
| 7,194,313 | B2 | 3/2007 | Libbus |
| 7,212,855 | B1 * | 5/2007 | Kroll et al. ......................... 607/4 |
| 7,225,020 | B1 * | 5/2007 | Kroll et al. ....................... 607/14 |
| 7,233,821 | B2 | 6/2007 | Hettrick et al. |
| 7,299,093 | B2 | 11/2007 | Zhu et al. |
| 7,319,900 | B2 | 1/2008 | Kim et al. |
| 7,337,000 | B2 | 2/2008 | Meyer et al. |
| 7,392,086 | B2 | 6/2008 | Sathaye |
| 7,499,751 | B2 | 3/2009 | Meyer et al. |
| 2002/0133203 | A1 * | 9/2002 | Mouchawar et al. ........... 607/11 |
| 2003/0083708 | A1 | 5/2003 | Bradley et al. |
| 2003/0208241 | A1 | 11/2003 | Bradley et al. |
| 2004/0039422 | A1 * | 2/2004 | Russie et al. ....................... 607/9 |
| 2004/0064162 | A1 | 4/2004 | Manrodt et al. |
| 2004/0082975 | A1 * | 4/2004 | Meyer et al. .................... 607/27 |
| 2004/0116971 | A1 * | 6/2004 | Bjorling et al. ................... 607/9 |
| 2004/0215253 | A1 | 10/2004 | Weinberg |
| 2004/0230229 | A1 | 11/2004 | Lovett |
| 2005/0060002 | A1 | 3/2005 | Zhu et al. |
| 2005/0060007 | A1 | 3/2005 | Goetz |
| 2005/0131476 | A1 | 6/2005 | Kim et al. |
| 2005/0131477 | A1 | 6/2005 | Meyer et al. |
| 2006/0074454 | A1 | 4/2006 | Freeberg |
| 2006/0129193 | A1 | 6/2006 | Zhang |
| 2006/0129194 | A1 * | 6/2006 | Zhang ............................. 607/17 |
| 2006/0129195 | A1 | 6/2006 | Sathaye et al. |
| 2006/0129196 | A1 | 6/2006 | Dong et al. |
| 2006/0129197 | A1 | 6/2006 | Zhang et al. |
| 2006/0129198 | A1 | 6/2006 | Zhang et al. |
| 2006/0129199 | A1 | 6/2006 | Zhang et al. |
| 2006/0241711 | A1 | 10/2006 | Sathaye |
| 2006/0247693 | A1 | 11/2006 | Dong et al. |
| 2006/0247695 | A1 | 11/2006 | Stalsberg et al. |
| 2006/0247696 | A1 * | 11/2006 | Stalsberg et al. ................. 607/9 |
| 2007/0255321 | A1 | 11/2007 | Gerber et al. |
| 2008/0046019 | A1 | 2/2008 | Sathaye et al. |
| 2008/0071318 | A1 | 3/2008 | Brooke et al. |
| 2008/0294215 | A1 | 11/2008 | Sathaye |
| 2008/0300644 | A1 | 12/2008 | Sathaye |
| 2009/0043352 | A1 | 2/2009 | Brooke et al. |

OTHER PUBLICATIONS

U.S. Appl. No. 12/154,411, filed May 22, 2008, Sathaye.
U.S. Appl. No. 12/220,496, filed Jul. 24, 2008, Brooke.
U.S. Appl. No. 11/114,569, filed Apr. 25, 2005, Sathaye.
U.S. Appl. No. 11/520,879, filed Apr. 14, 2006, Brooke et al.
U.S. Appl. No. 11/890,668, filed Aug. 7, 2007, Sathaye et al.
U.S. Appl. No. 11/116,544, filed Apr. 28, 2005, Meyer et al.
U.S. Appl. No. 11/116,578, filed Apr. 28, 2005, Stalsberg et al.
U.S. Appl. No. 11/116,558, filed Apr. 28, 2005, Dong et al.
U.S. Appl. No. 11/116,565, filed Apr. 28, 2005, Stalsberg et al.
U.S. Appl. No. 11/116,525, filed Apr. 28, 2005, Meyer et al.
Office Action dated Sep. 2, 2007 from U.S. Appl. No. 10/955,393, 11 pages.
Office Action Response submitted Apr. 21, 2008 to office action dated Sep. 2, 2007 from U.S. Appl. No. 10/955,393, 12 pages.
Office Action dated Jul. 31, 2008 from U.S. Appl. No. 10/955,393, 8 pages.
Office Action Response with RCE submitted Dec. 22, 2008 to office action dated Jul. 31, 2008 from U.S. Appl. No. 10/955,393, 9 pages.
Office Action dated Mar. 20, 2009 from U.S. Appl. No. 10/955,393, 10 pages.
Interview Summary dated May 22, 2009 from U.S. Appl. No. 10/955,393, 4 pages.
Office Action Response submitted Jun. 9, 2009 to office action dated Mar. 20, 2009 from U.S. Appl. No. 10/955,393, 10 pages.
Notice of Allowance dated Sep. 2, 2009 from U.S. Appl. No. 10/955,393, 5 pages.

* cited by examiner

CAPTURE DETECTION WITH CROSS CHAMBER BACKUP PACING

FIELD OF THE INVENTION

The present invention relates generally to cardiac devices and methods, and, more particularly, to devices and methods for detecting capture of a cardiac chamber with backup pacing delivered to a contralateral cardiac chamber.

BACKGROUND OF THE INVENTION

When functioning normally, the heart produces rhythmic contractions and is capable of pumping blood throughout the body. The heart has specialized conduction pathways in both the atria and the ventricles that enable excitation impulses (i.e. depolarizations) initiated from the sino-atrial (SA) node to be rapidly conducted throughout the myocardium. These specialized conduction pathways conduct the depolarizations from the SA node to the atrial myocardium, to the atrio-ventricular (AV) node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and/or coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver stimulation to the heart in accordance with various therapies for treating cardiac arrhythmias and dysynchronies.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to "capture" the heart tissue by generating a propagating depolarization wave that results in a contraction of the heart chamber. It is desirable for a pace pulse to have sufficient energy to stimulate capture of the heart chamber without expending energy significantly in excess of the capture threshold. Thus, accurate determination of the capture threshold is required for efficient pace energy management. If the pace pulse energy is too low, the pace pulses may not reliably produce a contractile response in the heart chamber and may result in ineffective pacing. If the pace pulse energy is too high, the patient may experience discomfort and the battery life of the device will be shorter.

Detecting if a pacing pulse captures the heart allows the pacemaker to adjust the energy level of pace pulses to correspond to the optimum energy expenditure that reliably produces capture. Further, capture detection allows the pacemaker to initiate a backup pulse whenever a pace pulse does not produce a contraction. This backup pulse is typically designed to ensure capture.

It is desirable to deliver the backup pace to maintain pacing support for the patient without interfering with the evoked response signal used for capture detection. The present invention provides methods and systems for capture detection with backup pacing providing various advantages over the prior art.

SUMMARY OF THE INVENTION

The present invention involves methods and systems for detecting capture of a heart chamber with backup pacing in a contralateral heart chamber. A method in accordance with one embodiment involves delivering a pacing pulse to a first heart chamber. A cardiac signal of the first heart chamber is sensed following delivery of the pacing pulse. The cardiac response to the pacing pulse is classified based on one or more features of the sensed cardiac signal. A backup pacing pulse is delivered to a second heart chamber contralateral to the first heart chamber, wherein the timing of the backup pacing pulse is based on the timing of the features used to classify the cardiac pacing response.

According to one approach, the backup pacing pulse is delivered relative to an expected timing of the features used to classify the cardiac pacing response. According to another approach, the backup pacing pulse is delivered relative to a detected timing of the features used to classify the cardiac pacing response. A scheduled backup pace may be inhibited if capture is detected.

Sensing the cardiac signal may involve sensing the cardiac signal during a detection interval which may be initiated following a delay after the pacing pulse or immediately after the pacing pulse. The backup pacing pulse may be delivered before, during or after the detection interval.

In some implementations, the backup pacing pulse is delivered at an energy previously used for pacing the contralateral heart chamber. For example, in one implementation, the energy of the backup pacing pulse is not increased from a previously used level.

Another embodiment of the invention is directed to a cardiac rhythm management system. The system includes pacing circuitry configured to deliver a pacing pulse to a first cardiac chamber and to deliver a backup pacing pulse to a cardiac chamber contralateral to the first cardiac chamber. Sensing circuitry is configured to sense a cardiac signal of the first chamber following the pacing pulse delivered to the first chamber. Capture detection circuitry classifies the cardiac response of the first chamber based on one or more features of the sensed cardiac signal. Backup pacing timing circuitry times the delivery of the backup pacing pulse based on the timing of the one or more features. In some implementations, the backup pace is inhibited if capture is detected.

In one configuration, the first chamber is a first ventricle and the contralateral chamber is the ventricle contralateral to the first ventricle. In another configuration, the first chamber is a first atrium and the contralateral chamber is the atrium contralateral to the first atrium.

In various implementations, the timing circuitry may be configured to time the delivery of the backup pacing pulse relative to an expected timing or a detected timing of the features used to classify the cardiac pacing response.

In some implementations, the capture detection circuitry is configured to sense for the one or more features used for capture detection during a detection interval. The backup pace is delivered during the detection interval.

Another embodiment is directed to a method of performing capture detection with backup pacing. A pacing pulse is delivered to a first heart chamber. The cardiac signal of the first heart chamber is sensed within a detection interval following delivery of the pacing pulse. The cardiac response is classified as a captured response based on one or more features of the sensed cardiac signal. A backup pace is delivered to a second heart chamber contralateral to the first heart chamber within the detection interval.

Yet another embodiment of the invention is directed to the energy use for backup pacing. A pacing pulse is delivered to a first heart chamber. A cardiac signal is sensed following delivery of the pacing pulse. The cardiac response to the pacing pulse is determined based on one or more features of the sensed cardiac signal. A backup pacing pulse is delivered to a second heart chamber contralateral to the first heart chamber. The backup pacing pulse has an energy previously determined for pacing the contralateral chamber.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
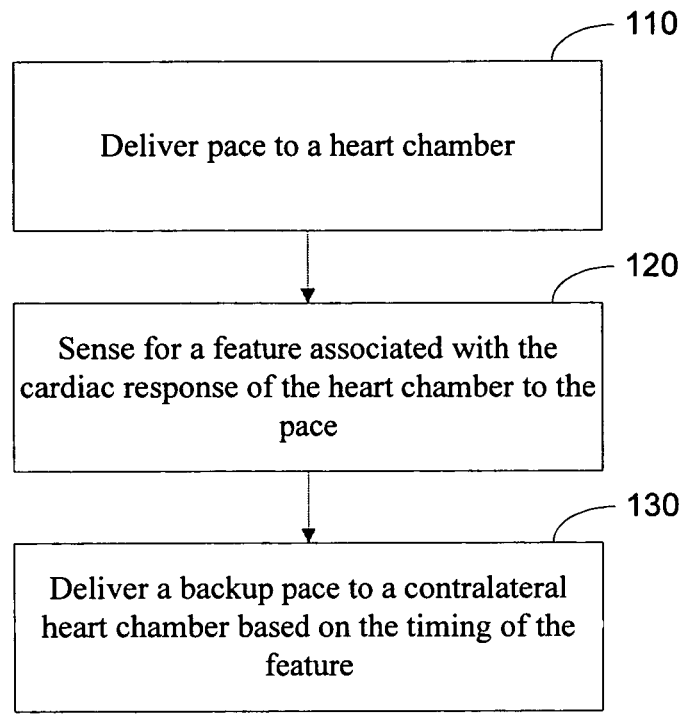
FIGS. 1A and 1B are flowcharts illustrating a methods for capture detection in a first cardiac chamber with backup pacing delivered to a contralateral cardiac chamber in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Synchronized pacing of contralateral heart chambers has been shown to be an effective treatment for patients with congestive heart failure (CHF). Typically, pacing energy is delivered to the heart tissue via one or more cathode electrodes with a return path provided via one or more anode electrodes. If capture occurs, the energy injected at the cathode electrode site creates a propagating wavefront of depolarization that triggers a contraction of the cardiac muscle.

The pacing energy required to capture the heart chamber may be determined by a capture threshold test. For example, a capture threshold test may step down the pacing energy for successive pacing cycles until loss of capture is detected. In other implementations, the capture threshold test may involve a step-up capture threshold test, a binary search test, or other capture threshold testing methods as are known in the art. The capture threshold of a pacing site may change over time due to various physiological effects. Testing the capture threshold for a particular pacing site or chamber may be implemented periodically or on command to ensure that the pacing energy delivered to the cardiac chamber remains sufficient to produce capture.

In systems that pace multiple chambers the capture threshold for each paced chamber may be individually tested. During a capture threshold test for a particular chamber or during therapeutic pacing, it is desirable to maintain pacing support through backup pacing. For example, backup pacing may be delivered after every pace during a capture threshold test. Backup pacing has previously been delivered to the test chamber at a fixed interval following the delivery of the test pace. Typically backup pacing is delivered at a relatively high energy to ensure capture.

It should be noted that capture threshold testing is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a backup safety pace to ensure consistent pacing. If a predetermined number of pace pulses delivered during normal pacing do not produce a captured response, the pacemaker may initiate a capture threshold test to determine the capture threshold. Aspects of the capture detection approaches of the present invention involving pacing in one chamber and backup pacing in a contralateral chamber may be useful for capture threshold testing and also for beat-to-beat automatic capture detection.

High energy backup pacing has several disadvantages. For example, pacemakers are typically powered by a battery and pacing at a fixed, high energy level depletes energy reserves of the battery more quickly. In addition, high energy backup pacing may interfere with detection of capture by the primary or test pace. Determination of the cardiac pacing response may be accomplished by sensing the cardiac signal following delivery of the pace and determining if signal features indicative of an evoked response are present in the signal. Signal features indicative of a particular cardiac pacing response, e.g., evoked response, fusion, or a non-captured/intrinsic response, may include, for example, positive or negative peaks exceeding a threshold or other morphological features of the cardiac signal occurring within a time interval relative to the delivery of the pacing pulse. High energy backup pacing delivered to the primary or test chamber may cause increased morphology instability in the cardiac signal due to the destabilization of the lead-tissue interface.

The present invention is directed to methods and systems for delivering backup pacing while extending battery lifetime and avoiding destabilization of the lead-tissue interface. According to the approaches of the present invention, backup paces are delivered to a heart chamber contralateral to the primary or test chamber. Backup pacing in the contralateral chamber serves to reduce the effect of the backup pace on the signal morphology of the primary or test chamber. Alternatively or additionally, backup pacing may be delivered without increasing the energy of the backup pace beyond the energy used for pacing which is known to produce capture. In addition, delivery of the backup paces may be coordinated with sensing for determining the cardiac pacing response to avoid interference between the backup pace and cardiac signal features used in the capture detection process. Timing the delivery of backup pacing according to the approaches of the present invention provides enhanced flexibility with respect to implementing blanking periods that are used in conjunction with pacing.

The flow chart of FIG. 1A illustrates a method for capture detection with backup pacing in accordance with embodiments of the invention. A pace is delivered 110 to a primary or test heart chamber. The system senses 120 for one or more cardiac signal features indicating the cardiac response to the pacing pulse. A backup pace is delivered 130 to a heart chamber contralateral to the primary or test heart chamber. The timing of the backup pace depends on the timing of the one or more cardiac signal features indicative of the cardiac pacing response. The cardiac response to the primary or test pace is determined based on the cardiac signal features. In some implementations, a scheduled backup pace is inhibited if capture is detected.

In one approach, the timing of the delivered or scheduled but inhibited backup pace may depend on the expected timing of the one or more cardiac signal features indicative of the cardiac pacing response. For example, the backup pace may be delivered to the contralateral heart chamber before cardiac signal features indicative of capture, fusion or a non-captured/intrinsic response are expected to occur. In another implementation, a backup pace may be delivered or may be scheduled for delivery to the contralateral heart chamber after cardiac signal features indicative of capture, fusion or a non-captured/intrinsic response are expected to occur. Capture detection based on morphological analysis of cardiac signals relies on beat to beat consistency in the presentation of features associated with capture or other cardiac pacing responses. In some implementations, where feature timing is relatively consistent from beat to beat, the expected timing of the features used for cardiac response determination may be established by the system based on the previous cardiac cycles. In other words, for a particular patient, the system may "learn" to expect certain features to occur around a particular time after delivery of the pacing pulse based on the historical timing of the features over a number of previous cardiac cycles.

In another approach, the timing of the backup pace may depend on the timing of detected cardiac signal features used to determine the cardiac pacing response. For example, after one or more particular features associated with the cardiac pacing response are detected, e.g., the peak amplitude, the backup pace may be delivered at a time relative to the time of the detected features. Delivery of the backup pace after the features are detected ensures that the backup pace does not alter the morphological signature of the cardiac signal that is used to determine the cardiac pacing response.

In one embodiment, the system senses for one or more features indicative of the cardiac pacing response in a detection interval that follows the delivery of the pace to a primary or test chamber. Capture, fusion, noncapture, and/or non-capture with an intrinsic response may be determined based on cardiac signal features that occur within a detection interval. Determination of the cardiac response to pacing based on detected morphological features of the cardiac signal following pacing are described in more detail in the following commonly owned patent documents which are incorporated herein by reference: U.S. Publication Nos. 20050131476 and 20050131477 and U.S. patent application Ser. Nos. 11/116,544, 11/116,578, 11/116,558, 11/116,565, and 11/116,525 all filed on Apr. 28, 2005.

According to some embodiments, delivery of a backup pace may occur during the capture detection interval or may occur after the detection interval. For example, in one implementation, the timing of the backup pace is determined by a fixed interval timed from the primary/test pace, where the fixed interval is shorter than the detection interval. In this implementation, the backup pace is delivered during the capture detection interval. In another implementation, the fixed interval is longer than the capture detection interval causing the backup pace to be delivered after the capture detection interval. The ability to schedule the backup pace during or after the capture detection interval allows for optimal flexibility in managing blanking periods.

Figure 1B:
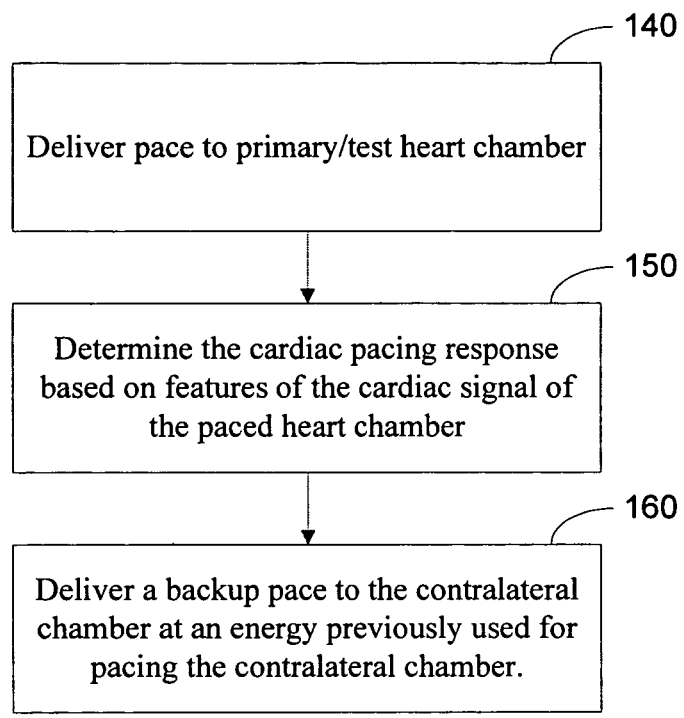

According to some approaches, the backup pace is delivered to the contralateral heart chamber at an energy level that was previously determined to be sufficient to effect capture of the contralateral chamber. This embodiment is illustrated by the flowchart of FIG. 1B. A pace is delivered 140 to a first heart chamber. The system determines 150 the cardiac response of the first heart chamber to the pace. A backup pace is delivered 160 to a heart chamber contralateral to the first heart chamber at an energy level previously determined sufficient for capture, such as the energy level currently used for normal pacing in the contralateral chamber. The backup pace may be delivered before, during or after the capture detection interval. The timing of the backup pace may be based on a fixed interval and/or may be adaptable based on the timing of expected or detected signal features used to determine the cardiac response of the first chamber to the pace. For example, the backup pace may be delivered within 0 to 500 ms following delivery of the pace to the first chamber.

Figure 2A:
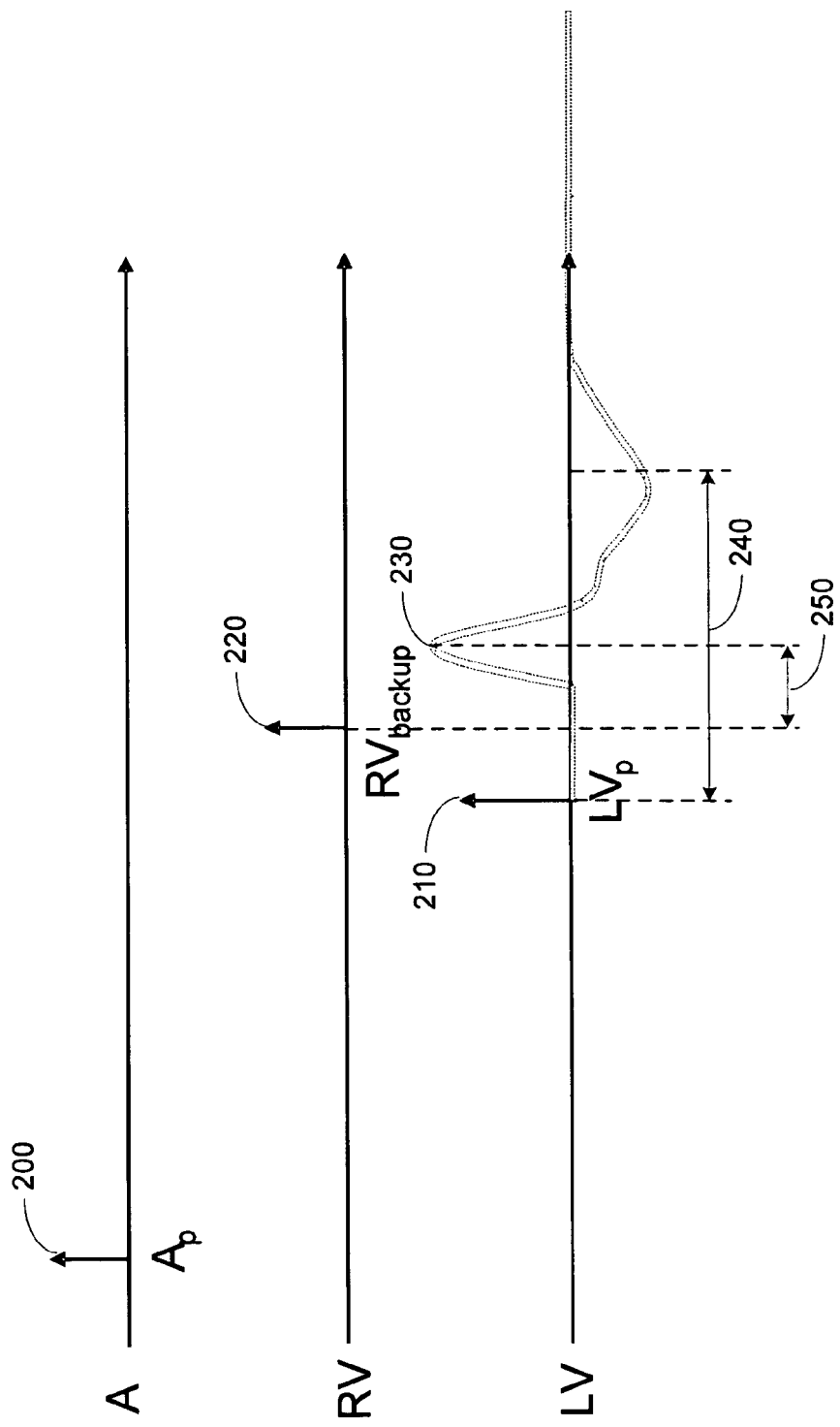
FIGS. 2A and 2B are timing diagrams illustrating backup pacing in a contralateral heart chamber based on the expected timing of a signal feature used to the determine the cardiac pacing response of a primary or test chamber in accordance with embodiments of the invention.
Figure 2B:
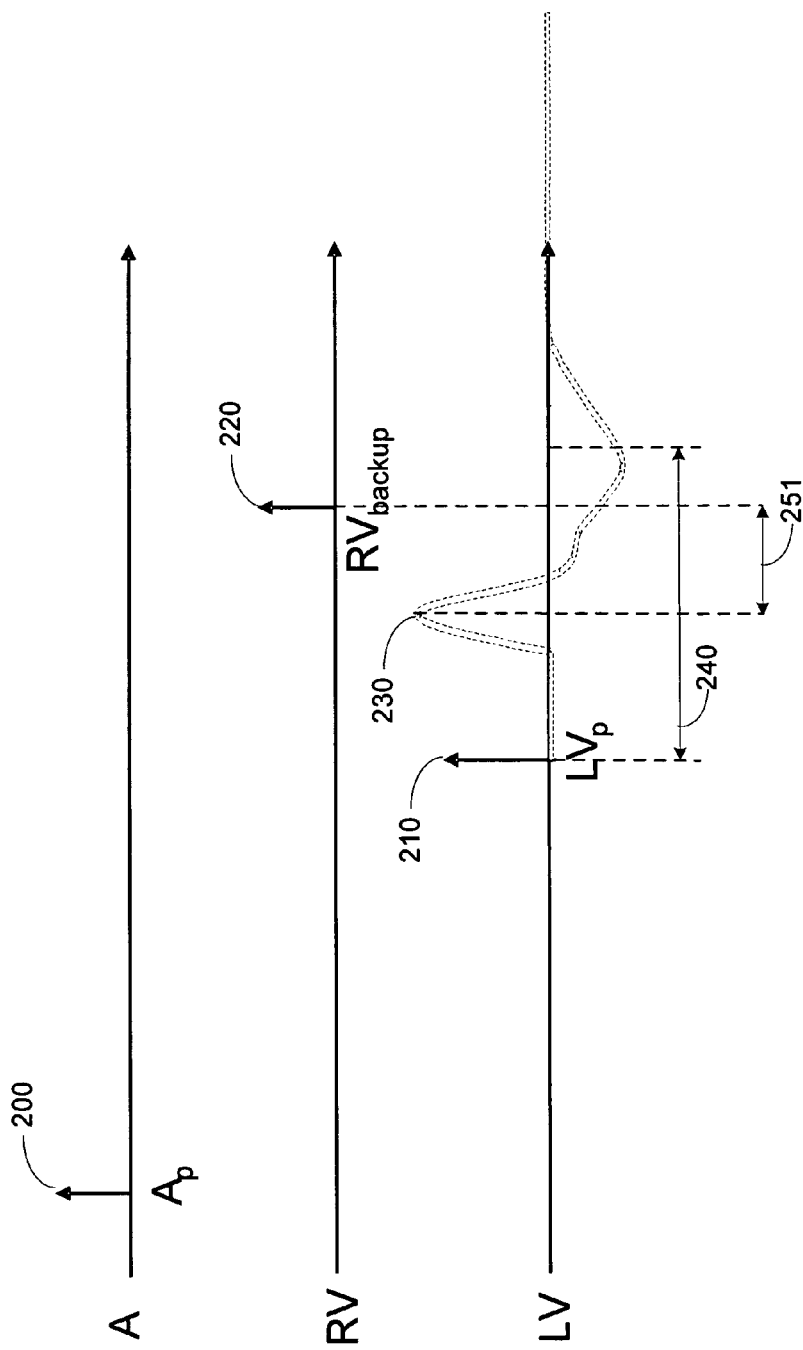

FIGS. 2A and 2B are timing diagrams for atrial (A), right ventricular (RV) and left ventricular (LV) channels illustrating delivery of a right ventricular backup pace based on the expected timing of a signal feature used to the determine the cardiac pacing response to a test pace delivered to the left ventricle. The processes illustrated in FIGS. 2A and 2B may be used for backup pacing during a capture threshold test to determine the left ventricular capture threshold. The cardiac cycle begins with a pace 200, Ap, delivered to an atrium. Following an atrioventricular delay (AVO), a test pacing pulse 210 is delivered to the left ventricle. A detection interval 240 is initiated following the left ventricular pace 210. During the detection interval 240, the system senses for a signal peak 230 indicative of the cardiac response to the left ventricular pace 210.

A backup pace 220 is delivered to the right ventricle. In FIG. 2A, the backup pace 220 is delivered prior to the time the peak 230 is expected to occur. In FIG. 2B, the backup pace is delivered after the time the peak 230 is expected to occur. The interval 250, 251 between the delivery of the right ventricular backup pace 220 and the expected signal peak 230 may be selected so that the backup pace 220 does not destabilize the electrode-tissue interface at the site of the test pace electrode or otherwise interfere with detection of the peak 230.

Figure 3A:
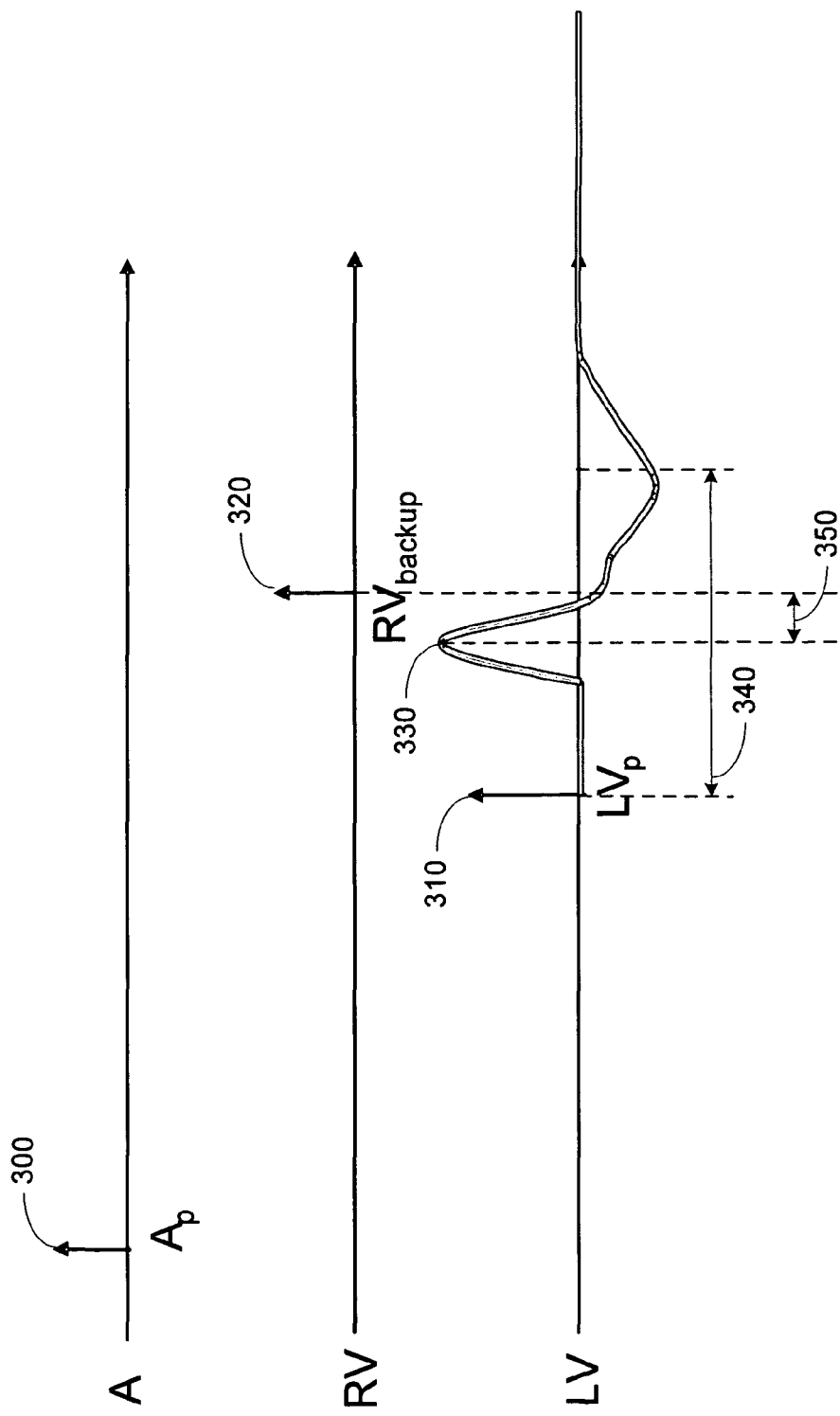
FIGS. 3A and 3B are timing diagrams illustrating backup pacing timed relative to a detected cardiac signal feature used for determining the cardiac response to pacing a primary or test cardiac chamber in accordance with embodiments of the invention.
Figure 3B:
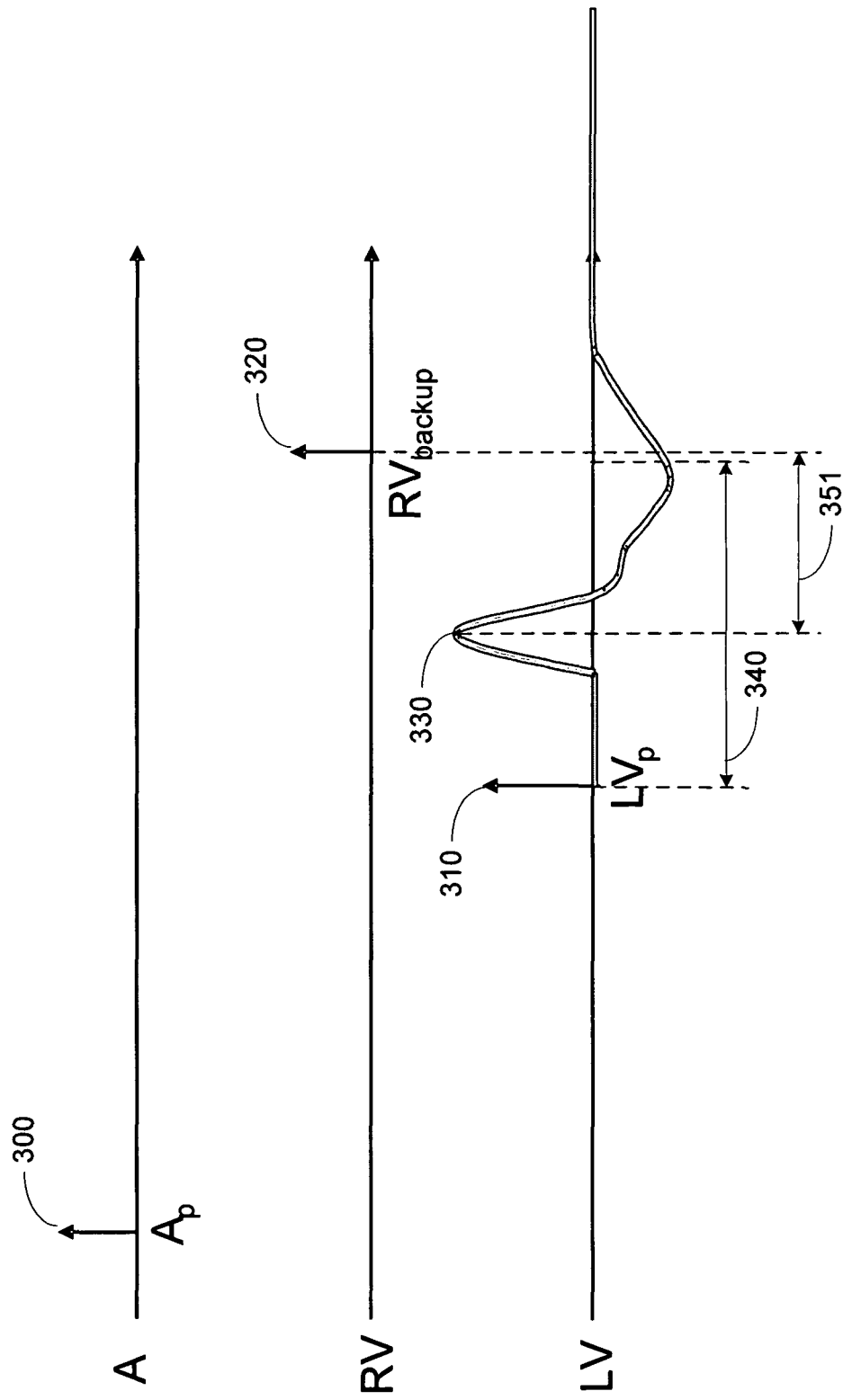

FIGS. 3A and 3B are timing diagrams illustrating backup pacing timed relative to a detected cardiac signal feature used for determining the cardiac response to pacing. The processes illustrated in FIGS. 2B, 3A and 3B may be used, for example, in conjunction with a capture threshold test to determine the capture threshold of the a ventricle, or may be used for automatic capture detection during normal pacing of the left ventricle. The cardiac cycle begins with an atrial pace 300, Ap, or a sensed atrial depolarization.

Following an AVD timed relative to the atrial pace or sensed atrial depolarization, a pacing pulse 310 is delivered to the left ventricle. A detection interval 340 is initiated following the left ventricular pace 310. During the detection interval 340, the system senses for a signal peak 330 indicative of the cardiac response to the left ventricular pace 310.

A backup pace 320 is delivered to the right ventricle. In the case of a capture threshold test, the backup pace 320 may be delivered regardless of the capture determination with respect to the left ventricular pace 310. If the process is used for automatic capture detection during normal pacing, the backup pace 320 may be delivered only if the left ventricular pace 310 fails to capture the left ventricle. The backup pace 320 is delivered following detection of the signal feature 330 that indicates the cardiac pacing response. The signal feature 330 may be analyzed to determine if the signal feature 330 corresponds to a pacing artifact rather than to a pacing artifact plus an evoked response. If only the pacing artifact is present in the signal feature 330, noncapture of the left ventricle is indicated and the backup pace 320 is delivered.

FIG. 3A illustrates delivery of the backup pace 320 during the detection interval 340. In FIG. 3B, the backup pace 320 is delivered after the detection interval 340. In these embodiments, the backup pace occurs following intervals 350, 351 after the detection of the signal feature 330 used for cardiac pacing response determination. Thus, the backup pace 320 does not alter the morphology of the cardiac signal used for cardiac response determination and does not interfere with detection of the feature 330.

It will be appreciated that although the examples provided by FIGS. 2A-2B and FIGS. 3A-3B are based on primary or test paces delivered to the left ventricle with backup paces delivered to the right ventricle, the approach is equally applicable to primary or test paces delivered to the right ventricle with backup paces delivered to the left ventricle. In addition, the approaches described in FIGS. 2A-2B and FIGS. 3A-3B may be applied to delivery of primary or test paces to an atrium with backup paces delivered to the contralateral atrium.

Figure 4:
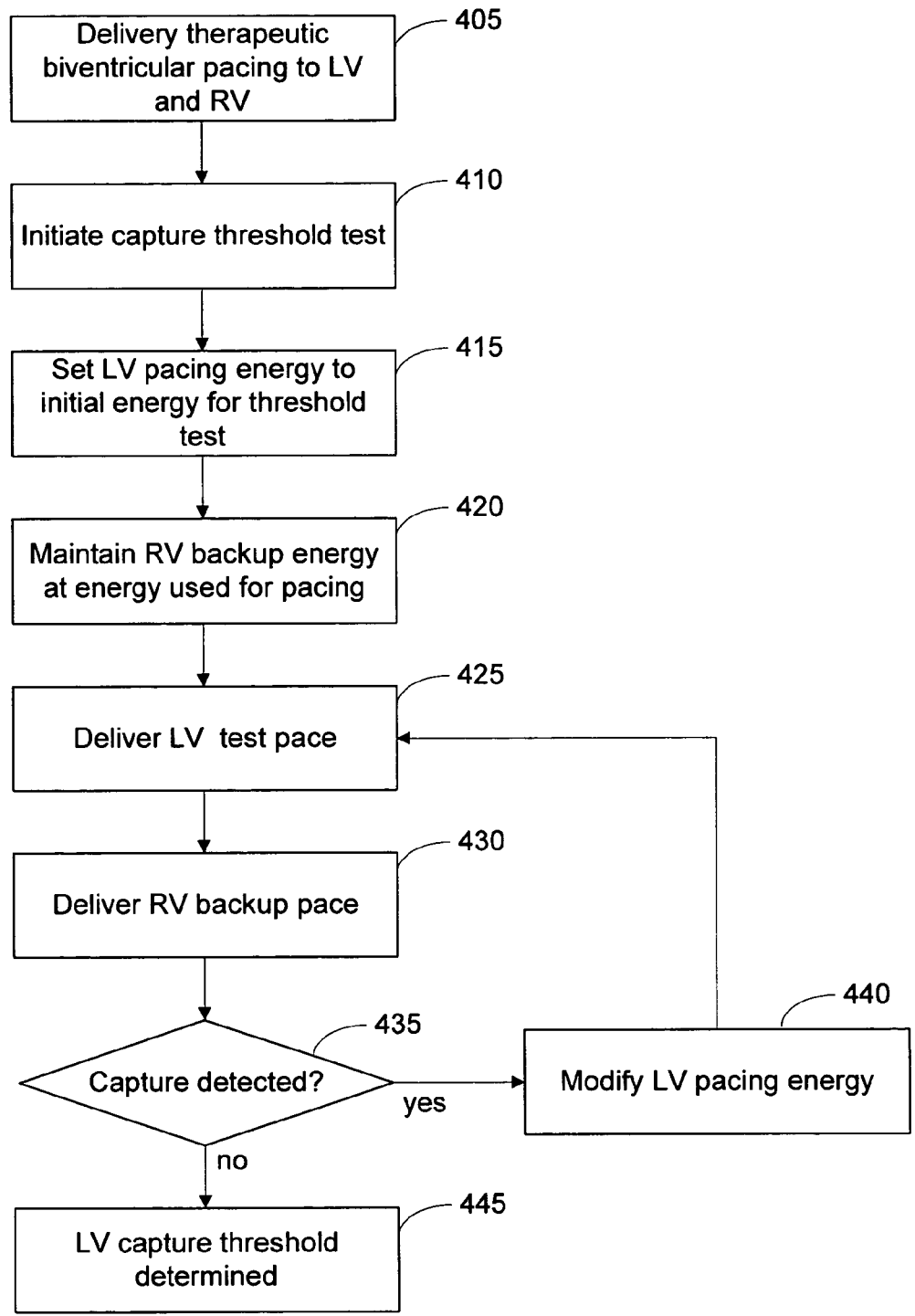
FIG. 4 is a flowchart illustrating a method for performing a capture threshold test with cross chamber backup pacing without increasing the energy of the backup pace in accordance with embodiments of the invention.

FIG. 4 illustrates a method for performing a capture threshold test in accordance with embodiments of the invention. In this example, the capture threshold of the left ventricle (LV) is determined with backup pacing delivered to the right ventricle (RV) during the test. The energy of the RV backup pace is maintained at an energy previously determined to exceed the capture threshold of the RV. A similar approach may be used for performing a capture threshold test for other heart chambers.

Prior to initiating the capture threshold test 410, biventricular pacing may be delivered 405 to the LV and RV at energy levels previously determined to capture the heart chambers. Periodically, on command or automatically, the pacemaker initiates 410 a capture threshold test to evaluate the capture threshold of one or more heart chambers. In this example, the LV capture threshold is tested and it is assumed that the pacing energy used for the RV is sufficient to produce capture. A step-down capture threshold test is described, although other methods for performing the capture threshold test, such as a step-up search, binary search, or other search methods may be employed and applied to the other heart chambers. The LV pacing energy is set 415 to an initially high pacing energy level. The RV pacing energy is maintained 420 at the previously determined pacing energy. An LV test pace and RV backup pace are delivered 425, 430. For each pacing cycle, the system determines 435 if capture occurs. If capture is detected 435, the LV pacing energy is decreased 440 and the test continues. If capture is not detected 435 the LV capture threshold is determined 445.

Figure 5:
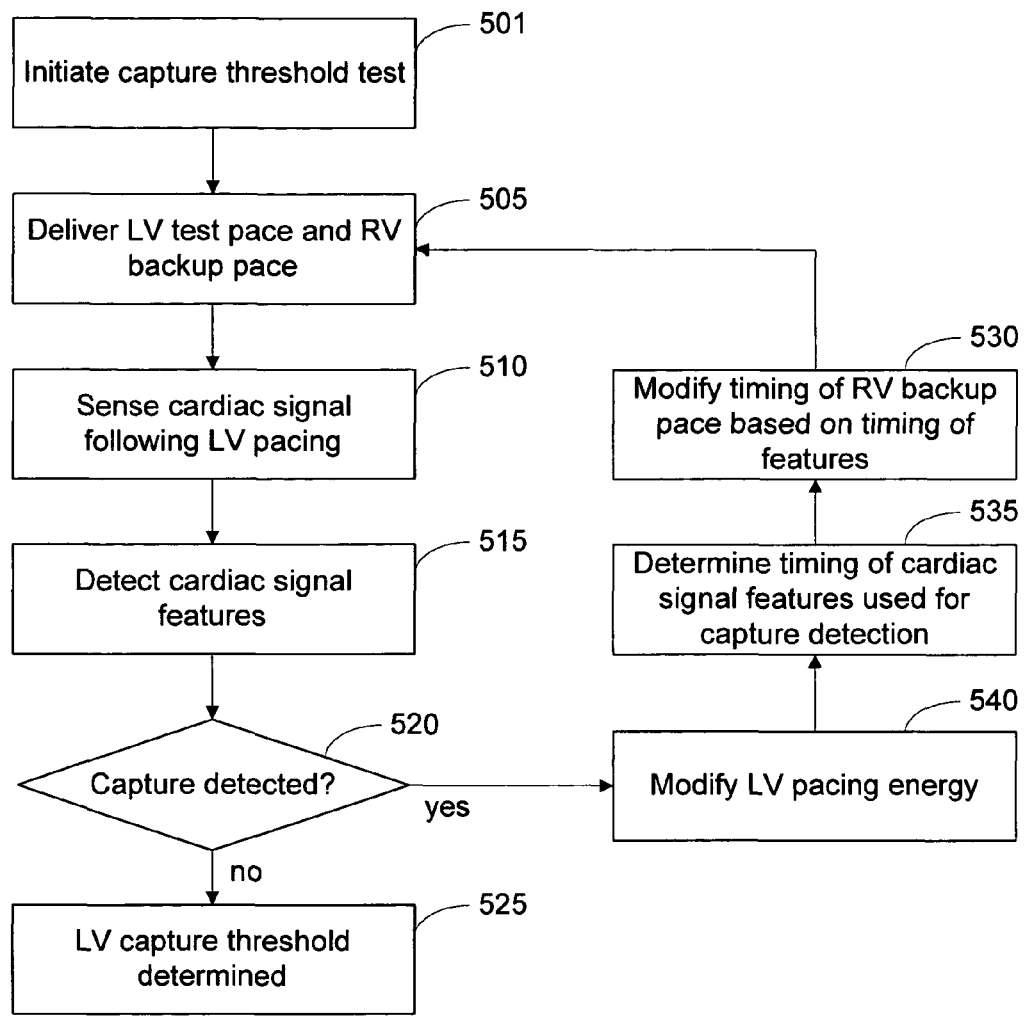
FIG. 5 is a flowchart illustrating a method for performing a capture threshold test with cross chamber backup pacing where the timing of the backup pace relative to the test pace is modified during the test based on cardiac signal features used for capture detection in accordance with embodiments of the invention.

The flowchart of FIG. 5 illustrates another process for performing capture threshold testing using cross chamber backup pacing in accordance with embodiments of the invention. As described in connection with FIG. 4, the system may periodically initiate 501 a capture threshold test to determine the capture threshold of a selected chamber. The test described in FIG. 5 is a step-down test for determining the capture threshold of the LV with RV backup pacing, although the process is equally applicable to other types of capture threshold tests and/or other heart chambers.

A test pace is delivered 505 to the LV and a backup pace is delivered 505 to the RV. The system senses 510 the LV cardiac signal following delivery of the LV test pace and detects 515 cardiac signal features associated with capture of the LV. Based on the signal features, the system may discriminate between capture or non capture of the LV. If capture is not detected 520, the capture threshold is determined 525.

If capture is detected 520, the LV pacing energy is decreased. The timing of the cardiac signal feature or features used for capture detection is determined 535. The timing of the RV backup pace relative to the LV test pace is modified 530 based on the timing of the cardiac signal features used for capture detection. Modification of the timing of the RV backup pace with respect to the LV test pace may be accomplished, for example, by modifying the interventricular delay between the LV and RV paces. The test continues using the modified RV backup pace timing and LV pace energy.

Figure 6:
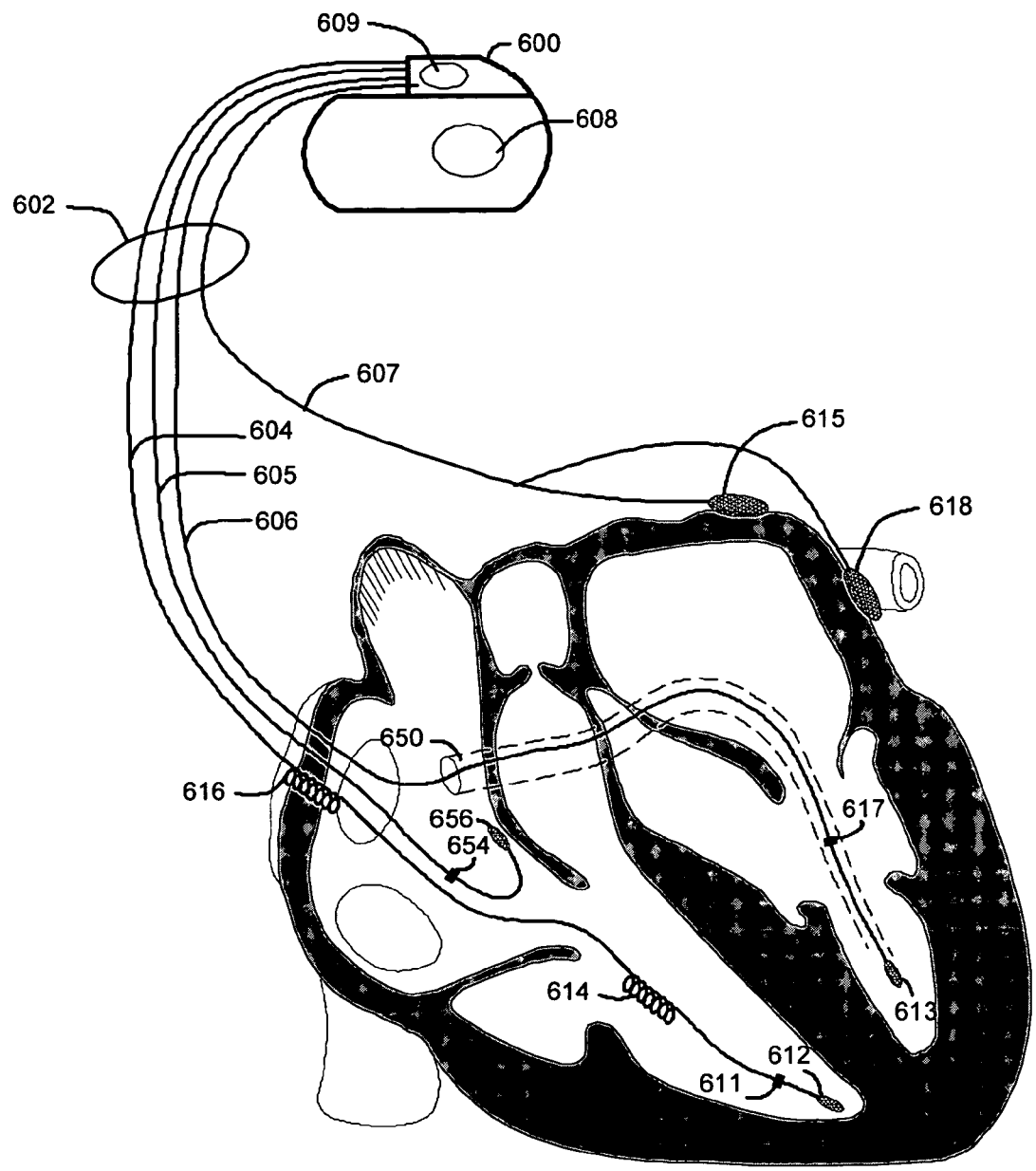
FIG. 6 shows a cardiac rhythm management system that may be used to implement capture detection with backup pacing in accordance with the approaches of the present invention.

Referring now to FIG. 6 of the drawings, there is shown a cardiac rhythm management (CRM) system that may be used to implement capture detection with backup pacing in accordance with the approaches of the present invention. The CRM system in FIG. 6 includes a pacemaker 600 (or optionally a pacemaker/defibrillator) enclosed within a housing and coupled to a lead system 602. The housing and/or header of the pacemaker 600 may incorporate one or more can or indifferent electrodes 608, 609 used to provide electrical stimulation energy to the heart and/or to sense cardiac electrical activity. The pacemaker 600 may utilize all or a portion of the pacemaker housing as a can electrode 608. The pacemaker 600 may include an indifferent electrode 609 positioned, for example, on the header or the housing of the pacemaker 600. If the pacemaker 600 includes both a can electrode 608 and an indifferent electrode 609, the electrodes 608, 609 typically are electrically isolated from each other.

The lead system 602 is used to detect cardiac electrical signals produced by the heart and to provide electrical energy to the heart under certain predetermined conditions to treat cardiac arrhythmias. The lead system 602 may include one or more electrodes used for pacing, sensing, and/or defibrillation. In the embodiment shown in FIG. 6, the lead system 602 includes an intracardiac right ventricular (RV) lead system 604, an intracardiac right atrial (RA) lead system 605, and an intracardiac left ventricular (LV) lead system 606. An extracardiac left atrial (LA) lead system 607 is employed.

The CRM system illustrated in FIG. 6 is configured for biventricular or biatrial pacing. The lead system 602 of FIG. 6 illustrates one embodiment that may be used in connection with the capture detection processes described herein. Other leads and/or electrodes may additionally or alternatively be used. For example, the CRM system may pace multiple sites in one cardiac chamber via multiple electrodes within the chamber. This type of multisite pacing may be employed in one or more of the right atrium, left atrium, right ventricle or left ventricle. Multisite pacing in a chamber may be used for example, to increase the power and or synchrony of cardiac contractions of the paced chamber.

The lead system 602 may include intracardiac leads 604, 605, 606 implanted in a human body with portions of the intracardiac leads 604, 605, 606 inserted into a heart. The intracardiac leads 604, 605, 606 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 6, the lead system 602 may include one or more extracardiac leads 607 having electrodes 615, 618, e.g., epicardial electrodes, positioned at locations outside the heart for sensing and pacing one or more heart chambers. In some configurations, the epicardial electrodes may be placed on or about the outside of the heart and/or embedded in the myocardium from locations outside the heart.

The right ventricular lead system 604 illustrated in FIG. 6 includes an SVC-coil 616, an RV-coil 614, an RV-ring electrode 611, and an RV-tip electrode 612. The right ventricular lead system 604 extends through the right atrium and into the right ventricle. In particular, the RV-tip electrode 612, RV-ring electrode 611, and RV-coil electrode 614 are positioned at appropriate locations within the right ventricle for sensing and delivering electrical stimulation pulses to the heart. The SVC-coil 616 is positioned at an appropriate location within the right atrium chamber of the heart or a major vein leading to the right atrial chamber.

In one configuration, the RV-tip electrode 612 referenced to the can electrode 608 may be used to implement unipolar pacing and/or sensing in the right ventricle. Bipolar pacing and/or sensing in the right ventricle may be implemented using the RV-tip 612 and RV-ring 611 electrodes. In yet another configuration, the RV-ring 611 electrode may optionally be omitted, and bipolar pacing and/or sensing may be accomplished using the RV-tip electrode 612 and the RV-coil 614, for example. The right ventricular lead system 604 may be configured as an integrated bipolar pace/shock lead. The RV-coil 614 and the SVC-coil 616 are defibrillation electrodes.

The left ventricular lead 606 includes an LV distal electrode 613 and an LV proximal electrode 617 located at appropriate locations in or about the left ventricle for pacing and/or sensing the left ventricle. The left ventricular lead 606 may be guided into the right atrium of the heart via the superior vena cava. From the right atrium, the left ventricular lead 606 may be deployed into the coronary sinus ostium, the opening of the coronary sinus 650. The lead 606 may be guided through the coronary sinus 650 to a coronary vein of the left ventricle. This vein is used as an access pathway for leads to reach the surfaces of the left ventricle which are not directly accessible from the right side of the heart. Lead placement for the left ventricular lead 606 may be achieved via subclavian vein access and a preformed guiding catheter for insertion of the LV electrodes 613, 617 adjacent to the left ventricle.

Unipolar pacing and/or sensing in the left ventricle may be implemented, for example, using the LV distal electrode referenced to the can electrode 608. The LV distal electrode 613 and the LV proximal electrode 617 may be used together as bipolar sense and/or pace electrodes for the left ventricle. The lead system 602 in conjunction with the pacemaker 600 may provide bradycardia pacing therapy to maintain a hemodynamically sufficient heart rate. The left ventricular lead 606 and the right ventricular lead 604 and/or the right atrial lead and the left atrial lead may be used to provide cardiac resynchronization therapy such that the ventricles and/or atria of the heart are paced substantially simultaneously or in phased sequence separated by an interventricular or interatrial pacing delay, to provide enhanced cardiac pumping efficiency for patients suffering from congestive heart failure.

The right atrial lead 605 includes a RA-tip electrode 656 and an RA-ring electrode 654 positioned at appropriate locations in the right atrium for sensing and pacing the right atrium. In one configuration, the RA-tip 656 referenced to the can electrode 608, for example, may be used to provide unipolar pacing and/or sensing in the right atrium. In another configuration, the RA-tip electrode 656 and the RA-ring electrode 654 may be used to effect bipolar pacing and/or sensing.

Figure 7:
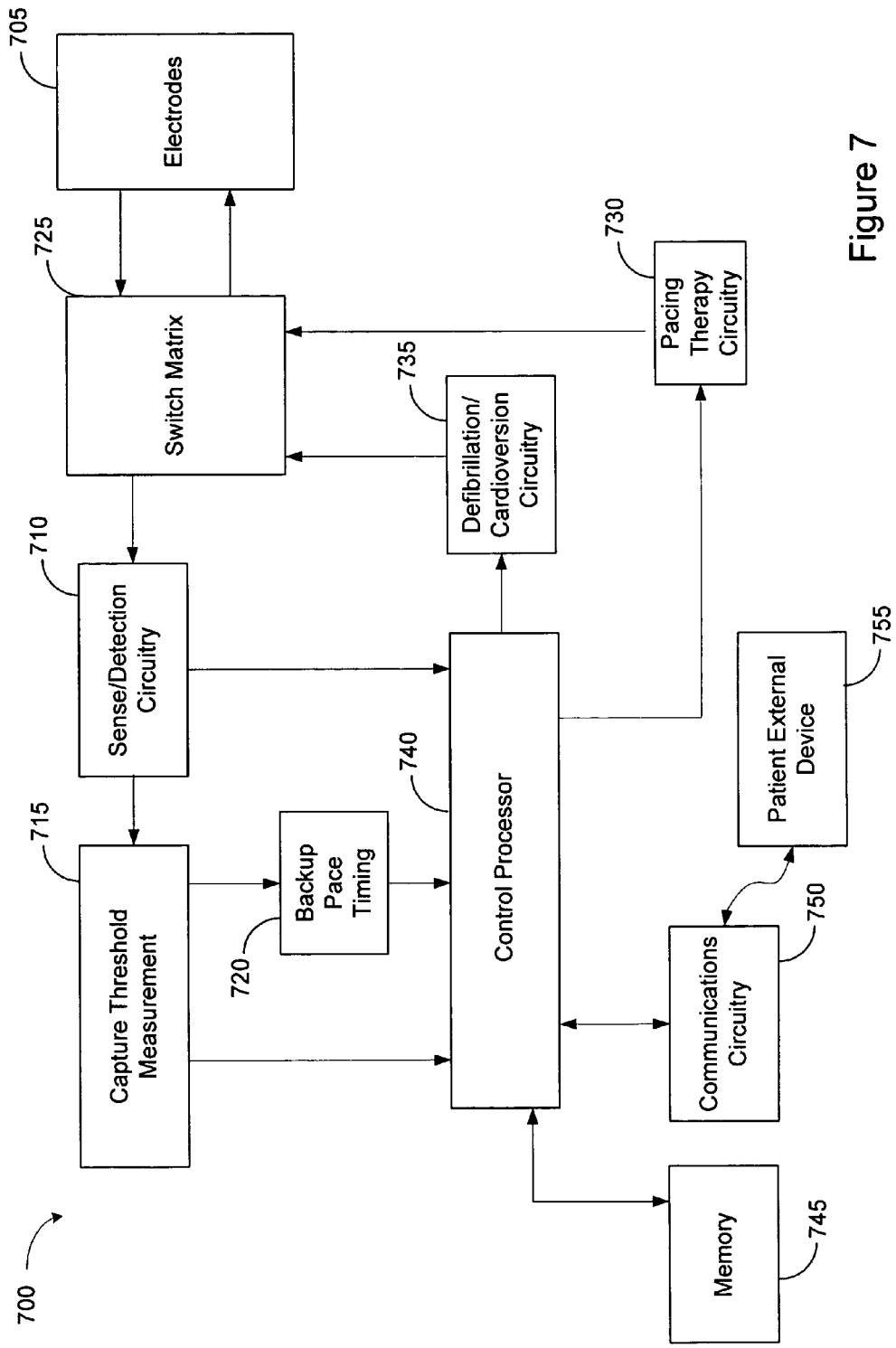
FIG. 7 illustrates a block diagram of an implantable cardiac rhythm management system suitable for implementing capture detection and backup pacing in accordance with embodiments of the invention.

Referring now to FIG. 7, there is shown a block diagram of an embodiment of an implantable CRM system 700 suitable for implementing capture detection and backup pacing approaches of the present invention. FIG. 7 shows a CRM system 700 divided into functional blocks. It is understood by those skilled in the art that there exist many possible configurations in which these functional blocks can be arranged. The example depicted in FIG. 7 is one possible functional arrangement. Other arrangements are also possible. For example, more, fewer or different functional blocks may be used to describe a cardiac system suitable for implementing the capture detection processes of the present invention. In addition, although the CRM system 700 depicted in FIG. 7 contemplates the use of a programmable microprocessor-based logic circuit, other circuit implementations may be utilized.

The CRM system 700 includes a control processor 740 capable of controlling the delivery of pacing pulses or defibrillation shocks to the right ventricle, left ventricle, right atrium and/or left atrium. The pacing therapy circuitry 730 is configured to generate pacing pulses for treating bradyarrhythmia, for example, or for synchronizing the contractions of contralateral heart chambers using biatrial and/or biventricular pacing.

The control processor 740 may also include an arrhythmia detector that operates to detect atrial or ventricular tachyarrhythmia or fibrillation. Under control of the control processor 740, the cardioversion/defibrillation circuitry 735 is capable of generating high energy shocks to terminate the tachyarrhythmia episodes.

The pacing pulses and/or defibrillation shocks are delivered via multiple cardiac electrodes 705 electrically coupled to a heart and disposed at multiple locations within, on, or about the heart. One or more electrodes 705 may be disposed in, on, or about each heart chamber or at multiple sites of one heart chamber. The electrodes 705 are coupled to switch matrix 725 circuitry that is used to selectively couple the electrodes 705 to the sense circuitry 710 and the therapy circuitry 730, 735.

The CRM system 700 includes capture detection circuitry 715 configured to detect capture or other responses to cardiac pacing, such as through morphological analysis of a cardiac signal that follows a pacing pulse. In some embodiments, the capture detection circuitry 715 is capable of discriminating capture from noncapture. In some embodiments, the capture detection circuitry 715 is further capable of detecting fusion beats and/or intrinsic noncaptured beats and/or discriminating one or both of these types of cardiac responses from a captured response.

Capture detection may be implemented by the capture detection circuitry 715 during capture threshold testing and/or during normal therapeutic pacing. The capture detection circuitry 715 may initiate a detection interval during which the cardiac signal following a pace pulse is sensed. The cardiac signal is analyzed for evidence of morphological features indicative of an evoked response and/or other types of cardiac pacing responses. Capture detection is used in conjunction with backup pacing. In embodiments related to capture threshold testing, a backup pace may be delivered after every test pace. In embodiments related to automatic capture detection, a backup pace may be delivered only when the primary pace fails to capture the heart chamber. In various embodiments, as previously described, the backup pace is delivered to a chamber contralateral to the chamber receiving the test or primary pace.

Timing of the backup pace is determined by backup pace timing circuitry 720. For example, the timing circuitry 720 may determine the timing of the backup pace based on the expected or detected cardiac signal features indicative of the cardiac response to a pacing pulse. The timing circuitry 720 may determine the timing of the backup pace as a fixed interval from the delivery of the primary or test pace. In some implementations, the backup pace may be delivered during the detection interval used for capture detection. In some implementations, the backup pace may be delivered at an energy previously used for pacing the chamber to which the backup pace is delivered. In other words, the energy of the backup pace is not necessarily increased from a previous energy level used to pace the chamber.

The CRM system 700 is typically powered by an electrochemical battery (not shown). A memory 745 stores data and program commands used to implement the capture detection and backup pacing approaches described herein along with other features. Data and program commands may be transferred between the CRM system 700 and a patient-external device 755 via telemetry-based communications circuitry 750.

Approaches for capture detection with backup pacing described herein may advantageously be used to select the timing, energy, and/or location of the backup paces to minimize the effect of the backup pacing on the cardiac signal used for classifying the cardiac pacing response. These embodiments may be used in systems capable of pacing a second site other than the capture detection site. The primary or test pacing site may be in a ventricular or atrial chamber with a backup pacing site in a contralateral ventricular chamber or contralateral atrial chamber. The approaches described herein serve to simplify the behavior of capture detection algorithms by removing additional steps required to account for signal morphology differences that may occur due to destabilization of the lead-tissue interface of the capture site by the backup pace.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of performing capture detection with backup pacing, comprising:
    delivering a pacing pulse to a first heart chamber;
    sensing a cardiac signal having one or more evoked response features of the first heart chamber following delivery of the pacing pulse, the one or more evoked response features indicative of the response of the first heart chamber to the pacing pulse;
    classifying a cardiac response to the pacing pulse based on the one or more evoked response features of the sensed cardiac signal;
    determining a timing of the one or more evoked response features;
    determining a timing for delivery of a backup pacing pulse, the timing for delivery of the backup pacing pulse is dependent on the determined timing of the one or more evoked response features; and
    delivering the backup pacing pulse to a second heart chamber contralateral to the first heart chamber based on the determined timing for delivery of the backup pacing pulse, wherein delivering the pacing pulse, sensing, classifying, determining the timing of the one or more evoked response features, determining the timing for delivery of the backup pacing pulse, and delivering the backup pacing pulse occur within each of a plurality of sequential cardiac cycles and are each performed at least in part by circuitry of a medical device.

2. The method of claim 1, wherein the determining of the timing of the one or more evoked response features comprises determining an expected timing of the one or more evoked response features.

3. The method of claim 1, wherein the determining of the timing of the one or more evoked response features comprises determining a detected timing of the one or more evoked response features.

4. The method of claim 1, wherein sensing the cardiac signal of the first heart chamber following delivery of the pacing pulse comprises sensing the cardiac signal during a detection interval.

5. The method of claim 4, wherein the backup pacing pulse is delivered before or during the detection interval based on the determined timing for delivery.

6. The method of claim 4, wherein the backup pacing pulse is delivered after the detection interval based on the determined timing for delivery.

7. The method of claim 1, wherein the backup pacing pulse is delivered at an energy previously used for pacing the contralateral heart chamber.

8. The method of claim 1, wherein an energy of the backup pacing pulse is not increased from a previously used level.

9. The method of claim 1, wherein delivering the pacing pulse to the first heart chamber, sensing the cardiac signal, classifying the cardiac response to the pacing pulse, determining the timing of the one or more evoked response features, determining the timing for delivery of the backup pacing pulse, and delivering the backup pacing pulse to the second heart chamber are performed as part of a capture threshold test.

10. The method of claim 1, wherein classifying the cardiac response to the pacing pulse comprises classifying the cardiac response as one of capture, non-capture, or fusion associated with delivery of the pacing pulse to the first chamber.

11. The method of claim 1, wherein:
determining the timing of the one or more evoked response features comprises determining the expected timing of sensing of the one or more evoked response features of the cardiac signal;
determining the timing for delivery of the backup pacing pulse comprises determining a time interval between delivery of the backup pacing pulse and the expected sensing of the one or more evoked response features of the cardiac signal; and
delivering the backup pacing pulse comprises delivering the backup pacing pulse, separated in time by the time interval, before the expected timing of sensing of the one or more evoked response features of the cardiac signal.

12. The method of claim 1, wherein:
determining the timing of the one or more evoked response features comprises determining the timing of sensing of the one or more evoked response features of the cardiac signal;
determining the timing for delivery of the backup pacing pulse comprises determining a time interval between sensing of the one or more evoked response features of the cardiac signal and delivery of the backup pacing pulse; and
delivering the backup pacing pulse comprises delivering the backup pacing pulse at expiration of the time interval initiated at the determined time of sensing of the one or more evoked response features of the cardiac signal.

13. The method of claim 1, wherein:
determining the timing of the one or more evoked response features comprises determining an expected timing of sensing of the one or more evoked response features of the cardiac signal; and
determining the timing for delivery of the backup pacing pulse comprises determining a time for delivery that is before the one or more evoked response features are expected.

14. The method of claim 1, wherein:
determining the timing of the one or more evoked response features comprises determining a detected timing of sensing of the one or more evoked response features of the cardiac signal; and
determining the timing for delivery of the backup pacing pulse comprises determining a time for delivery that is after the detected timing of sensing of the one or more evoked response features.

15. The method of claim 1, wherein the one or more evoked response features comprises a signal peak indicative of ventricular depolarization of the first heart chamber.

16. The method of claim 1, further comprising delivering an atrial pace to an atrial chamber, wherein the pacing pulse is delivered to the first heart chamber following expiration of a predetermined atrioventricular delay.

17. The method of claim 1, further comprising initiating a detection interval following delivery of the pacing pulse to the first heart chamber, wherein content of the cardiac signal within the detection interval is analyzed to detect the one or more evoked response features.

18. The method of claim 1, further comprising modifying a pacing energy parameter of the pacing pulse, wherein:
modifying the pacing energy parameter is performed for each of the plurality of cardiac cycles until capture no longer occurs based on the classifying of the cardiac response.

19. The method of claim 1, wherein the first heart chamber is a left ventricle and the second heart chamber is a right ventricle.

20. The method of claim 1, wherein the determining of the timing of the one or more evoked response features is based on timing of sensing of previous evoked response features associated with pacing pulses previously delivered to the first heart chamber.

21. A method for timing delivery of contralateral backup pacing pulses, the method comprising:
delivering a plurality of pacing pulses to a first heart chamber over a plurality of cardiac cycles, one pacing pulse of the plurality of pacing pulses delivered for each cardiac cycle of the plurality of cardiac cycles;
determining timing of each of a plurality of evoked responses, each evoked response of the plurality associated with delivery of a respective one of the plurality of pacing pulses;
delivering a plurality of backup pacing pulses over the plurality of cardiac cycles, each backup pulse of the plurality delivered to a heart chamber contralateral to the first heart chamber for a respective one of the plurality of cardiac cycles; and
varying timing of the delivery of the plurality of backup pacing pulses based on the timing of the plurality of evoked responses, wherein delivering the pacing pulses, determining timing, delivering the backup pacing pulses, and varying are each performed at least in part by circuitry of a medical device.

22. The method of claim 21, further comprising modifying a pacing energy parameter of the pacing pulse, wherein modifying the pacing energy parameter is performed for each of the plurality of cardiac cycles until capture no longer occurs.

23. A method of performing capture detection with backup pacing, comprising:
delivering a pacing pulse to a first heart chamber;
sensing a cardiac signal having one or more evoked response features of the first heart chamber following delivery of the pacing pulse, the one or more evoked response features indicative of the response of the first heart chamber to the pacing pulse;
classifying a cardiac response to the pacing pulse based on the one or more evoked response features of the sensed cardiac signal;

determining a timing of the one or more evoked response features;
determining a timing for delivery of a backup pacing pulse, the timing for delivery of the backup pacing pulse is dependent on the determined timing of the one or more evoked response features;
delivering the backup pacing pulse to a second heart chamber contralateral to the first heart chamber based on the determined timing for delivery of the backup pacing pulse, wherein delivering the pacing pulse, sensing, classifying, determining the timing of the one or more evoked response features, determining the timing for delivery of the backup pacing pulse, and delivering the backup pacing pulse are each performed for each of a plurality of cardiac cycles and are each performed at least in part by circuitry of a medical device; and
modifying a pacing energy parameter of the backup pacing pulse, wherein modifying the pacing energy parameter is performed for each of the plurality of cardiac cycles until capture no longer occurs based on the classifying of the cardiac response.

* * * * *